United States Patent [19]
Karim et al.

[11] Patent Number: 6,028,221
[45] Date of Patent: Feb. 22, 2000

[54] CATALYST SYSTEMS FOR THE ONE STEP GAS PHASE PRODUCTION OF ACETIC ACID FROM ETHYLENE AND METHODS OF MAKING AND USING THE SAME

[75] Inventors: Khalid Karim, Manchester, United Kingdom; Kareemudin Sheikh, Riyadh, Saudi Arabia

[73] Assignee: Saudi Basic Industries Corporation, Saudi Arabia

[21] Appl. No.: 09/107,046

[22] Filed: Jun. 29, 1998

[51] Int. Cl.$^7$ .................................................. C07C 51/16
[52] U.S. Cl. ............................................................. 562/548
[58] Field of Search ............................................. 562/548

[56] References Cited

U.S. PATENT DOCUMENTS

| | | | |
|---|---|---|---|
| 3,057,915 | 10/1962 | Riemenschneider et al. | 260/533 |
| 3,131,223 | 4/1964 | Smidt et al. . | |
| 3,240,805 | 3/1966 | Naglieri | 260/533 |
| 3,301,905 | 1/1967 | Riemenschneider et al. | 260/597 |
| 4,148,757 | 4/1979 | Brazdil et al. | 252/432 |
| 4,250,346 | 2/1981 | Young et al. | 585/658 |
| 4,339,355 | 7/1982 | Decker et al. | 252/464 |
| 4,524,236 | 6/1985 | McCain | 585/658 |
| 4,568,790 | 2/1986 | McCain | 585/658 |
| 4,596,787 | 6/1986 | Manyik et al. | 502/312 |
| 4,899,003 | 2/1990 | Manyik et al. | 585/313 |
| 5,049,692 | 9/1991 | Hatano et al. | 558/319 |
| 5,162,578 | 11/1992 | McCain, Jr. et al. | 562/512.2 |
| 5,198,580 | 3/1993 | Bartek et al. | 562/542 |
| 5,300,682 | 4/1994 | Blum et al. | 562/512.2 |

FOREIGN PATENT DOCUMENTS

| | | | |
|---|---|---|---|
| 0 294 845 | 12/1988 | European Pat. Off. | 88/50 |
| 0 407 091 | 1/1991 | European Pat. Off. . | |
| 0 480 594 | 4/1992 | European Pat. Off. . | |
| 0 518 548 | 12/1992 | European Pat. Off. . | |
| 0 620 205 | 10/1994 | European Pat. Off. | 94/42 |
| 0 627 401 | 12/1994 | European Pat. Off. . | |
| 06293695 | 4/1993 | Japan . | |
| 98/05619 | 2/1998 | WIPO . | |

OTHER PUBLICATIONS

E.M. Thorsteinson et al. "The Oxidative Dehydrogenetion of Ethane . . . " *Journal of Catalysis* vol. 52, pp. 116–132 (1978).

*Primary Examiner*—Gary Geist
*Assistant Examiner*—Robert W. Deemie
*Attorney, Agent, or Firm*—Whitman Breed Abbott & Morgan LLP

[57] ABSTRACT

A mixed metal oxide catalytic system comprising MoVNbPd or MoLaVPd providing higher selectivity and space time yield of acetic acid in the low temperature single stage oxidation of ethylene with molecular oxygen-containing gas and steam with very minimum or without the production of side products such as acetaldehyde, and methods of using the same.

20 Claims, No Drawings

CATALYST SYSTEMS FOR THE ONE STEP GAS PHASE PRODUCTION OF ACETIC ACID FROM ETHYLENE AND METHODS OF MAKING AND USING THE SAME

RELATED APPLICATIONS

This application is related to U.S. application Ser. No. 08/997,913 filed Dec. 24, 1997, and U.S. application Ser. No. 09/107,115 filed concurrently herewith, by Karim et al., entitled "Catalysts for Gas Phase Production of Acetic Acid from Ethane, Processes of Making the Same and Methods of Using Same", herein incorporated by reference.

BACKGROUND OF THE INVENTION

1. Field of the Invention

This invention relates to improved catalytic systems, including MoVNbPd, MoVLaPd and combinations thereof, and to improved catalytic processes for the low temperature selective oxygenation of ethylene to acetic acid. More specifically, the invention relates to a single stage catalytic process using novel catalysts for providing high ethylene conversions and acetic acid yields.

2. Description of the Related Art

Several publications are referenced in this application. These references describe the state of the art to which this invention pertains, and are incorporated herein by reference.

Acetic acid is generally produced by methanol carbonylation using an expensive rhodium catalyst in a liquid phase homogeneous reaction. This method requires complicated procedures for the recovery of the catalyst and the isolation of the products. Moreover, the presence of iodine at ppm levels in the final product has a negative impact on the usage of the acetic acid produced by the method.

Acetic acid is also produced by a two stage acetaldehyde process using manganese catalysts. Such processes are disclosed in U.S. Pat. Nos. 3,131,223; 3,057,915; 3,301,905; and 3,240,805. The first stage of this process involves the production of acetaldehyde from ethylene. The economics of the process is not favored due to the costs arising from the two stages. Furthermore, these processes produce a large amount of acetaldehyde as a by-product. In addition, a large amount of ethylene may be lost by complete oxidation into carbon dioxide.

More recently, Showa Denko [EP 0 62 0205 A1] relates to a catalytic process for converting ethylene to acetic acid using catalysts containing heteropoly acids of phosphorus, silicon, boron, aluminum, germanium, titanium, zirconium, cerium, cobalt, chromium and metal palladium with at least one element selected from groups XI, XIV, XV, and XVI of the periodic table. The single pass conversion of ethylene was reported to be very low over these heteropoly catalysts and produces a significant amount of acetaldehyde, which can have a great impact on the separation cost. The catalytic systems used in the present invention are different from the Showa Denko catalysts.

EP A 0 29 4845 relates to a process for the higher selective production of acetic acid by the oxidation of ethane or ethylene with oxygen in contact with a physical mixture of at least two catalyst systems consisting of (A) a catalyst for oxydehydrogenation of ethane to ethylene and (B) a catalyst for hydration/oxidation of ethylene. The ethane oxydehydrogenation catalyst is represented by the formula $Mo_xV_yZ_z$, wherein Z can be one or more of the metals Nb, Sb, Ta, Ca, Sr, Ti, W, Li, Na, Be, Mg, Zn, Cd, Hg, Sc, Fe and Ni. The catalyst for hydration/oxidation is selected from a molecular sieve catalyst, a palladium-containing oxide catalyst, tungsten-phosphorus oxide catalyst, or tin or molybdenum containing oxide catalyst. EP A 0 29 4845 employs the catalyst prepared by the physical mixing of the two types of catalysts.

Japanese Patent No. 46-6763 relates to the catalytic oxidation of ethylene to acetic acid using specific catalysts disclosed in the examples containing the following combination of metal atoms: V-Pd-Sb, V-Rh-Sb, V-Pd-P, V-Rh-P, V-Rh-As, V-Pd-As, Mo-Pd-Sb, Mo-Rh-Sb, Mo-Rh-As, and Mo-P-W-Pd-Rh-Sb.

Japanese Patent No. 54-57488 relates to the use of $NaPdH_2$-PMoV catalysts for the oxidation of ethylene to acetic acid.

Syoji Tan et al. [J. Catal., vol. 17, pp. 132–142, 1970] reported that olefins oxidize to ketones over the binary catalyst systems $Co_3O_4$-$MoO_3$ and $SnO_2$-$MoO_3$. The article discloses the formation of acetic acid as a by-product together with other compounds and product of specifically ethylene was only carbon dioxide.

Thus, none of the prior art discloses or suggests the advantages of the catalytic system disclosed in present invention for the selective production of acetic acid from ethylene using a catalyst which is a dual function catalyst and is designed in such way that it enhances the activation function as well as the selectivity to the desired product acetic acid.

OBJECTS OF THE INVENTION

It is an object of the invention to overcome the above-identified deficiencies.

It is another object of the invention to provide improved catalyst systems for the production of acetic acid.

It is yet another object of the invention to provide an improved method of making acetic acid with enhanced selectivity and yield of the desired product acetic acid.

It is a still further object of the invention to provide a method of making improved catalysts for the production of acetic acid.

The foregoing and other objects and advantages of the invention will be set forth in or apparent from the following description.

SUMMARY OF THE INVENTION

The present invention relates to the selective oxidation of ethylene with molecular oxygen to acetic acid in a gas phase reaction at relatively high levels of conversion, selectivity and productivity at temperatures ranging from 150° C. to 450° C. and at pressures of 1–50 bar. This is achieved by using a mixed metal oxides including MoVNbPd or MoVLaPd oxide catalysts, supported or unsupported, such as those disclosed in related U.S. application Ser. No. 08/997,913 filed Dec. 24, 1997 and U.S. application Ser. No. 09/107,115, filed concurrently herewith.

DESCRIPTION OF THE PREFERRED EMBODIMENTS

For oxidation catalysts, the selectivity behavior to desired partial oxidation products depends on the types of active centers in the catalysts in addition to other physical reaction parameters, such as (a) hydrocarbon to oxygen ratio, (b) pressure, (c) reaction temperature, and (d) contact time.

Generally, it is well known that selectivity to mild oxygenated products such as acetic acid increases as reaction temperature decreases, whereas yield is decreased on account of total conversion. Active sites involved in the reaction play a key role in the direction of the reactions. Furthermore, the selectivity for the partial oxidation products depends on the reactivity of lattice oxygen to form C—O bonds with the adsorbed hydrocarbon. For example, alkenes are more reactive and adsorb preferentially as compared to alkanes over metal oxide/acidic catalysts. Mixed metal oxide phases of MoV are known to be responsible for the activation of hydrocarbon and the activity of the catalyst depends on the relative number of $V^{+4}$ and $V^{+5}$ over the surface of the catalyst. Moreover, palladium is known as a total oxidation metal, as well as a metal that helps to facilitate the oxygenation of alkene. An optimum amount of Pd with a high degree of dispersion of metal over mixed metal oxide catalyst results in a high selectivity to acetic acid.

Furthermore, it has been discovered that the addition of water as a co-feed plays an important role as a reaction diluent and as a heat moderator for the reaction and also acts as a desorption accelerator of the reaction product in the vapor phase oxidation reaction or masking the sites responsible for the total oxidation resulting in an increased yield of acetic acid.

In carrying out the partial oxidation of ethylene process, the reaction mixture preferably contains one mole of ethylene, 0.01 to 2.0 moles of molecular oxygen (either as pure oxygen or in the form of air), and zero to 5.0 moles of water in the form of steam. Other gases may be used as reaction diluents or heat moderators such as helium, nitrogen, and carbon dioxide.

The gaseous components of the reaction mixture preferably include ethylene, oxygen and a diluent, and these components may be uniformly admixed prior to being introduced into the reaction zone. The components may also be preheated, individually or after being admixed prior to being introduced into the reaction zone, which reaction zone should have a temperature of from about 150° C. to about 450° C.

The reaction zone preferably has a pressure of from 1 to 50 bar, more preferably from 1 to 30 bar; a temperature of from about 150° C. to about 450° C., more preferably from 200° C. to 300° C.; a contact time between the reaction mixture and the catalyst of from about 0.01 second to 100 seconds, more preferably from 0.1 second to 10 seconds; and a space hourly velocity of from about 50 to about 50,000 $h^{-1}$, more preferably from 100 to 10,000 $h^{-1}$ and most preferably from 200 to 3,000 $h^{-1}$.

The contact time is defined as the ratio between the apparent volume of the catalyst bed and the volume of the gaseous reaction mixture feed to the catalyst bed under the given reaction conditions in a unit of time.

The space velocity is calculated by determining total reactor outlet gas equivalent, in liters, of the total effluent evolved over a period of one hour divided by the liters of catalyst in the reactor. This room temperature volume is converted to the volume at 0° C. at 1 bar.

The reaction pressure is initially provided by the feed of the gaseous reactants and diluent and after the reaction has commenced, may be maintained by the use of a suitable back-pressure controller placed on the reactor outlet stream.

The reaction temperature may be provided by placing the catalyst bed within a tubular converter having walls placed in a circulating sand bath furnace heated to the desired reaction temperature.

The oxygen concentration in the feed gas mixture can vary widely, from 0.1 to 50% or higher of the feed mixture by applying proper measures to avoid explosion problems. Air is the preferred source of oxygen in the feed. The amount of oxygen present may be a stoichiometric amount, or lower, of the hydrocarbons in the feed.

The process is generally carried out in a single stage with all the oxygen and reactants being supplied as a single feed with non-reacted initial reactants being recycled. However, multiple stage addition of oxygen to the reactor with an intermediate hydrocarbon feed can also be used. This may improve productivity to acetic acid and avoid potentially hazardous conditions.

EXAMPLES

The following examples are illustrative of some of the products and methods of making the same falling within the scope of the present invention. They are, of course, not to be considered in any way limitative of the invention. Numerous changes and modifications can be made with respect to the invention.

Several examples were carried out to demonstrate the invention using the two catalyst compositions given below.

Catalyst A

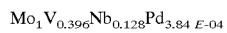

$Mo_1V_{0.396}Nb_{0.128}Pd_{3.84\ E\text{-}04}$

Catalyst B

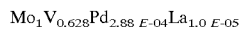

$Mo_1V_{0.628}Pd_{2.88\ E\text{-}04}La_{1.0\ E\text{-}05}$

Preparation Procedure for Catalyst A: Ammonium metavanadate (Aldrich Chemicals, Assay=99.0%) in the amount of 11.4 grams was added to 120 ml of distilled water and heated to 90° C. with stirring. 2.5 grams of oxalic acid were added to obtain a clear yellow color solution with a pH between 5 and 6 (Solution A). 19.4 grams of niobium oxalate (21.5% $Nb_2O_5$, Niobium Products Company, USA) were added to 86 ml of water and heated to 65° C. with continuous stirring to give a clear white color solution with a pH of 1 (Solution B). Solution B was then combined with Solution A. The resultant solution was heated at 90° C. and 28 grams of oxalic acid was added very slowly with continuous stirring to give Solution C. Ammonium paramolybdate tetra hydrated (Aldrich Chemicals A.C.S.—12054-85-2) in the amount of 43.2 grams was added to 45 ml of water and heated to 60° C. to give a colorless solution with a pH between 6.0 and 6.5 (Solution D). Solution D was combined slowly with Solution C to give dark blue to dark gray color precipitates (Mixture E). The required amount of palladium was added slowly to gel mixture. This dark color combination was stirred vigorously to achieve a homogeneous gel mixture which was then dried slowly to incipient dryness within 60 to 120 minutes at 95–98° C. with continuous stirring.

The resulting solid was put in a China dish and dried additionally in an oven at 120° C. for sixteen hours. The dried material was cooled to room temperature and placed in a furnace. The temperature was raised from room temperature to 350° C. at the rate of 2°/min. and thereafter held at 350° C. for four hours.

The calcined catalyst was formulated into uniform particles of the 40–60 mesh size and evaluated for the ethane oxidative dehydrogenation reaction.

Preparation Procedure for Catalyst B: Ammonium metavanadate (Aldrich Chemicals, Assay=99.0%) in the amount of 6 grams was added to 65 ml of distilled water and heated to 90° C. with stirring. 6 grams of oxalic acid was added to the above solution. The color of the solution changes from yellowish green to dark brown with a pH 2–2.5 at 80° C. (Solution A). Ammonium paramolybdate tetra hydrated (Aldrich Chemicals A.C.S.—12054-85-2) in the amount of 14.4 grams was added to 16.7 ml of water and heated to 60–65° C. to give a colorless solution with a pH between 5.0 and 6.0 (Solution B). Solution A was mixed slowly with Solution B to give dark blue to dark gray color precipitates (Mixture E). The required amount of palladium followed by lanthanum nitrate was added slowly to gel mixture. This dark color combination was stirred vigorously to achieve a homogeneous gel mixture which was then dried slowly to incipient dryness within 60 to 120 minutes at 95–98° C. with continuous stirring.

The resulting solid was put in a China dish and dried additionally in an oven at 120° C. for sixteen hours. The dried material was cooled to room temperature and placed in a furnace. The temperature was raised from room temperature to 350° C. at the rate of 2°/min and thereafter held at 350° C. for four hours.

The calcined catalyst was formulated into uniform particles of the 40–60 mesh size and evaluated for the ethane oxidative dehydrogenation reaction.

For Examples 1 to 5, catalyst A was used, while for Examples 6 and 7, catalyst B was used.

The reaction products were analyzed on-line by gas chromatography. Oxygen, nitrogen and carbon monoxide were analyzed using a 2.5 m by 3 mm column of 13× molecular sieve. Carbon dioxide and ethylene were analyzed using a 0.5 m by 3 mm column packed with material sold under the trade name PORAPACK™ N. Acetic acid and water were analyzed using a 1.5 m by 3 mm column packed with material sold under the trademark HAYASEP™ Q. In all cases, the conversion and selectivity calculations were based on the stoichiometry:

$$C_2H_4 + O_2 \rightarrow C_2H_4O_2$$

$$C_2H_4 + 2O_2 \rightarrow 2\ CO + 3\ H_2O$$

$$C_2H_4 + 3O_2 + \rightarrow 2\ CO_2 + 3\ H_2O$$

The yield of acetic acid was calculated by multiplying the selectivity to acetic acid by ethylene conversion.

Example 1

A stainless steel tubular reactor measuring 0.760 cm (inside diameter) by 46 cm (long) was charged with 1 g of calcined catalyst A (40–60 mesh) and diluted with 3 g of silicon dioxide of the same mesh size. The reactor was then heated to 285° C. in a sand bath thermostated furnace and pressurized to 200 psi with nitrogen. A gas feed containing 14.79% ethylene and 85.21% air, by volume, was fed to the reactor at a flow rate of 58.30 cc/min. The liquid products were condensed in a cold trap and the gas products were analyzed on an on-line GC system.

Example 2

A stainless steel tubular reactor measuring 0.760 cm (inside diameter) by 46 cm (long) was charged with 1 g of calcined catalyst A (40–60 mesh) and diluted with 3 g of silicon dioxide of the same mesh size. The reactor was then heated to 285° C. in a sand bath thermostat furnace and pressurized to 200 psi with nitrogen. A gas feed containing 14.94% ethylene and 85.06% air, by volume, was fed to the reactor at a flow rate of 60.40 cc/min. Water (8.85 cc/min. calculated as gas at STP) was also fed to the reactor inlet. The liquid products were condensed in a cold trap and the gas products were analyzed on an on-line GC system.

Example 3

A stainless steel tubular reactor measuring 0.760 cm (inside diameter) by 46 cm (long) was charged with 1 g of calcined catalyst A (40–60 mesh) and diluted with 3 g of silicon dioxide of the same mesh size. The reactor was then heated to 285° C. in a sand bath thermostat furnace and pressurized to 200 psi with nitrogen. A gas feed containing 15% ethylene and 85% air, by volume, was fed to the reactor at a flow rate of 91.33 cc/min. The liquid products were condensed in a cold trap and the gas products were analyzed on an on-line GC system.

Example 4

A stainless steel tubular reactor measuring 0.760 cm (inside diameter) by 46 cm (long) was charged with 1 g of calcined catalyst A (40–60 mesh) and diluted with 3 g of silicon dioxide of same mesh size. The reactor was then heated to 285° C. in a sand bath thermostat furnace and pressurized to 200 psi with nitrogen. A gas feed containing 15% ethylene and 85% air, by volume, was fed to the reactor at a flow rate of 90.60 cc/min. Water (9.17 cc/min calculated as gas at STP) was also fed to the reactor inlet. The liquid products were condensed in a cold trap and the gas products were analyzed on an on-line GC system.

Example 5

A stainless steel tubular reactor measuring 0.760 cm (inside diameter) by 46 cm (long) was charged with 7 g of calcined catalyst A (40–60 mesh) and diluted with 3 g of silicon dioxide of same mesh size. The reactor was then heated to 240° C. in a sand bath thermostat furnace and pressurized to 250 psi with nitrogen. A gas feed containing 10.10 ethylene and 89.9% air, by volume, was fed to the reactor at a flow rate of 35.33 cc/min. The liquid products were condensed in a cold trap and the gas products were analyzed on an on-line GC system.

Example 6

A stainless steel tubular reactor measuring 0.760 cm (inside diameter) by 46 cm (long) was charged with 1 g of calcined catalyst B (40–60 mesh) and diluted with 3 g of silicon dioxide of the same mesh size. The reactor was then heated to 285° C. in a sand bath thermostat furnace and pressurized to 200 psi with nitrogen. A gas feed containing 14.16% ethylene and 85.84% air, by volume, was fed to the reactor at a flow rate of 59.80 cc/min. Water (9.16 cc/min. calculated as gas at STP) was also fed to the reactor inlet. The liquid products were condensed in a cold trap and the gas products were analyzed on an on-line GC system.

Example 7

A stainless steel tubular reactor measuring 0.760 cm (inside diameter) by 46 cm (long) was charged with 1 g of calcined catalyst B (40–60 mesh) and diluted with 3 g of silicon dioxide of the same mesh size. The reactor was heated to 285° C. in a sand bath thermostat furnace and pressurized to 200 psi with nitrogen. A gas feed containing 14.31% ethylene and 85.69% air, by volume, was fed to the reactor at a flow rate of 59.90 cc/min. The liquid products were condensed in a cold trap and the gas products were analyzed on an on-line GC system.

The results of the tests with catalysts A & B under the reaction conditions described above are given in Table I and a typical analysis of the condensed product with impurities is given in Table II.

TABLE I

Ethylene Oxidation Data

| | Conversion (%) | | Selectivity (%) | | | Yield (%) | STY g.aa/l.cat/hr |
|---|---|---|---|---|---|---|---|
| Example | Ethylene | Oxygen | Acetic acid | CO | $CO_2$ | Acetic acid | Acetic acid |
| 1 | 62.87 | 97.68 | 61.07 | 3.72 | 34.45 | 38.5 | 635 |
| 2 | 77.33 | 98.25 | 77.82 | 0.96 | 19.83 | 60.18 | 1043 |
| 3 | 42.42 | 76.7 | 61.03 | 4.61 | 34.36 | 25.89 | 720 |
| 4 | 63.42 | 81.8 | 78.03 | 1.75 | 20.15 | 30.57 | 1291 |
| 5 | 98.63 | 87.71 | 65.11 | 0.33 | 34.56 | 64.22 | 70 |
| 6 | 86.14 | 98.44 | 80.00 | 1.40 | 18.60 | 68.9 | 1119 |
| 7 | 70.33 | 92.90 | 66.00 | 4.76 | 29.24 | 47 | 773 | g.aa/l.cat/hr. = grams acetic acid per liter catalyst per hr.

TABLE II

A Typical Analysis of Liquid Product.

| Component | wt % |
|---|---|
| Water | 30.37 |
| Acetic acid | 69.78 |
| Formaldehyde | 0.118 |
| Methyl acetate | 0.124 |
| Ethyl acetate | trace |
| acetaldehyde | trace |
| propionic acid | 0.06 |

From the above-described results exhibited using the invention, the following surprising and unexpected advantages may be derived:

1. High activity/conversion of ethylene reflects high rate of partial oxidation of alkene.
2. The invention provides a high rate of oxygenation of ethylene to acetic acid.
3. The invention provides a low rate of total oxidation to COx products.
4. The activity and selectivity to the oxygenation product, acetic acid, is increased while COx products are decreased with the addition of water into the feed and the magnitude of this impact depends on the amount of water used.

The above description of the invention is intended to be illustrative and not limiting. Various changes or modifications in the embodiments described may occur to those skilled in the art. These can be made without departing from the spirit or scope of the invention.

We claim:

1. A single step process for the selective oxidation of ethylene to acetic acid comprising the step of contacting a reaction mixture containing ethylene with oxygen or a compound capable of providing oxygen in a reaction zone in the presence of a calcined catalyst represented by the formula Mo-V-Nb-Pd-O or Mo-V-La-Pd-O under a reaction temperature sufficient to convert ethylene to acetic acid.

2. The process of claim 1, wherein said catalyst is in the form of a fixed or fluidized bed.

3. The process of claim 1, wherein said mixture further comprises steam.

4. The process of claim 1, wherein said reaction mixture further comprises air.

5. The process of claim 1, wherein said reaction mixture comprises oxygen.

6. The process of claim 1, wherein said mixture is a feed mixture introduced into said reaction zone.

7. The process of claim 1, wherein said mixture comprises molecular oxygen ranging from 0.1 to 50% by volume of the feed mixture.

8. The process of claim 1, wherein said mixture is diluted with water/steam in an amount ranging from 0 to 50% by volume of the feed mixture.

9. The process of claim 1, wherein said ethylene is in vapor form.

10. The process of claim 1, wherein the reaction temperature is from 150 to 450° C.

11. The process of claim 1, wherein said reaction zone under a pressure of from 1 to 50 bars.

12. The process of claim 1, wherein said contacting provides a contact time between said reaction mixture and the catalyst of from 0.1 to 10 seconds.

13. The process of claim 1, wherein said oxidation provides a 70% yield of acetic acid per single pass through said reaction zone.

14. The process of claim 1, wherein said oxidation provides a STY of 1400 (g. acetic acid/L. cat/hr) per single pass through said reaction zone.

15. The process of claim 1, wherein said oxidation of ethylene produces less than 5 ppm acetaldehyde.

16. The process of claim 1, wherein said mixture comprises greater than 10% by volume ethylene.

17. The process of claim 1, further comprising the multistage of introduction of air or oxygen into the reaction zone to increase the yield, selectivity or combination of yield and selectivity of acetic acid.

18. A process for performing a catalytic chemical reaction in fluid phase comprising the step of contacting a mixture containing at least one reactant in fluid phase with a calcined catalyst represented by the formula Mo-V-Nb-Pd-O or Mo-V-La-Pd-O under suitable reaction conditions.

19. The process of claim 18, wherein said catalytic chemical reaction converts one or more fluid phase reactants to one or more fluid phase products.

20. The process of claim 19, wherein said one or more fluid phase reactants comprise ethylene and said one or more fluid phase products comprise acetic acid.

* * * * *